United States Patent [19]

Treacy

[11] Patent Number: 5,542,947
[45] Date of Patent: Aug. 6, 1996

[54] SLOTTED PATELLA RESECTION GUIDE AND STYLUS

[75] Inventor: Patrick J. Treacy, Towaco, N.J.

[73] Assignee: Huwmedica Inc., New York, N.Y.

[21] Appl. No.: 440,290

[22] Filed: May 12, 1995

[51] Int. Cl.$^6$ ............................................... A61B 17/56
[52] U.S. Cl. .................................... 606/88; 606/87
[58] Field of Search ........................ 606/88, 87, 86, 606/89, 82, 80, 79, 96, 97, 102, 205, 206, 207

[56] References Cited

U.S. PATENT DOCUMENTS

| | | | |
|---|---|---|---|
| 4,633,862 | 1/1987 | Petersen | 606/88 |
| 4,706,660 | 11/1987 | Petersen | 606/86 |
| 4,759,350 | 7/1988 | Dunn et al. | 606/82 |
| 5,108,401 | 4/1992 | Insall et al. | 606/79 |
| 5,129,907 | 7/1992 | Heldreth et al. | 606/80 |
| 5,129,908 | 7/1992 | Petersen | 606/88 |
| 5,147,365 | 9/1992 | Whitlock et al. | 606/88 |
| 5,180,384 | 1/1993 | Mikhail | 606/80 |
| 5,197,986 | 3/1993 | Mikhail | 623/20 |
| 5,222,955 | 6/1993 | Mikhail | 606/80 |
| 5,295,992 | 3/1994 | Cameron | 606/79 |

Primary Examiner—Guy V. Tucker
Attorney, Agent, or Firm—Joseph J. Kaliko

[57] ABSTRACT

A slotted patella resection guide and stylus used in the preparation of the human patella to accept a patella prosthesis in total knee arthroplasty. The guide includes jaw members for gripping bone, the jaw members including a plurality of calibrated and marked steps (slots) located at a different fixed predetermined height above the desired resection level. Each slot accepts the stylus which may be at least temporarily secured therein. After determining the amount of bone to resect, the stylus is temporarily secured in the appropriate slot (marked as being calibrated to yield the amount of resection desired); and the guide is then clamped onto the patella at the location indicated by the guide/stylus combination, with the stylus resting on the patella in the area where its thickness was measured to establish the depth of cut. After the guide is clamped in position, a sagittal saw is inserted therein to actually perform the resection. During resection, the stylus may be removed from the guide to enhance visibility. The jaws of the guide include a saw capture slot which defines the plane of resection and accepts the saw blade to provide greater control of the cut during the operation. A saw blade insertion guide is also integrated into the resection guide to ease the process of inserting the blade into the capture slot and enhance safety characteristics of the instrument.

18 Claims, 3 Drawing Sheets

SLOTTED PATELLA RESECTION GUIDE AND STYLUS

BACKGROUND OF THE INVENTION

1. Field of the Invention

The invention relates generally to orthopedic surgical guides and jigs. More particularly, the invention relates to a slotted patella resection guide and stylus that may be used in the preparation of the human patella to accept a patella prosthesis in total knee arthroplasty. The slotted patella resection guide and stylus contemplated by the invention, when used in combination, enables the guide to be accurately placed at a level which assures a precise resection of a predetermined amount of bone.

According to a preferred embodiment of the invention, the resection guide has a plurality of calibrated and marked steps (slots), each located at a different fixed predetermined height above the desired resection level. Each slot is designed to accept the stylus which may be at least temporarily secured therein.

A surgeon, for example, once having determined the amount of bone to be resected, simply places and temporarily secures the stylus in the appropriate slot (the slot marked as being calibrated to yield the amount of resection desired); and then uses the resection guide contemplated herein, in a manner to be explained in detail hereinafter, to clamp onto the patella and guide a sagittal saw used to actually perform the resection.

Further aspects of the guide and stylus combination contemplated by the invention are (1) the quick attachment/release nature of the stylus itself, i.e, the stylus is easily attached to the calibrated and marked steps on the resection guide, and easily removable therefrom to enhance the surgeons visibility while performing the resection; (2) the jaws of the contemplated resection guide include a saw capture slot which defines the plane of resection and accepts the saw blade used to perform the resection, thereby providing greater control of the cut during the operation; and (3) a saw blade insertion guide mechanism is integrated into the patella resection guide. For example, the guide mechanism can take the form of a "ledge" where the saw blade enters the saw blade capture slot to ease the process of inserting the saw blade into the slot, provide support for the saw blade itself and enhance the safety characteristics of the instrument.

2. Description of the Related Art

The two largest and longest bones of the human body, the femur and tibia, meet at a person's knee. The tibia is situated at the front and inner side of the lower leg. It is prismoid in form, and expanded above where it enters into the knee joint. The head of the tibia is large and expanded on each side into two eminences, the condyles. These eminences form two smooth concave compartments or surfaces which articulate with the condyles of the femur. The medial condyle is more prominent anteriorly and broader both in the anterior-posterior and transverse diameters than the lateral condyle. Accordingly, the lateral articular surface of the tibia is shorter, more shallow and narrower than the medial surface of the tibia. The medial surface is broader, more circular, and concave from side to side. The anterior surfaces of the tuberosities are continuous with one another, forming a single large surface which is somewhat flattened. Posteriorly the tuberosities are separated from each other by a shallow depression for attachment of ligaments. The medial tuberosity presents posteriorly a deep transverse groove for the insertion of a tendon.

The patella is a sesamoid or lens shaped bone which slides in a groove between the condyles of the femur. Its function is to increase the efficiency of the quadriceps muscle by shifting the line of action of the muscle's pull forward. As the knee articulates, the muscles and tendons force the patella toward the condyles of the femur. Consequently, there is considerable relative motion between the patella and the other bones comprising the knee joint.

Because of aging or disease, the articulating surfaces of the knee may degrade. To treat certain pathologies, it has become common to surgically remove the condyles and replace these structures with prosthetic implants. By the same processes, the articulating surfaces of the patella may also degrade. In connection with the implantation of a prosthetic knee. therefore, the articulating surface of the patella may also be replaced. Because of the tendons connected to the patella, it is generally advisable to replace only the articulating surface. An ultra high molecular weight polyethylene articulating surface, with or without a metal baseplate, will be implanted on the posterior side of the patella, adjacent the femoral condyles.

To implant such a prosthesis, the posterior surface of the patella is resected to produce a flat surface upon which the prosthesis can be mounted. In the past, the surgeon often had to rely on skill of hand and eye in manipulating a sagittal saw in order to make an appropriate cut.

Prior art devices for aiding the surgeon in performing patella resections are well known to those skilled in the art.

For example, Petersen, in U.S. Pat. No. 4,633,862, issued Jan. 6, 1987, incorporated herein by reference, teaches a method and instruments for the installation of a patella button prosthesis which involves performing a patella resection.

In particular, Petersen describes a saw guide which comprises a pliers-like instrument having a pair of mutually pivotable jaw members. The jaw members are designed so as to enable them to surround the outer periphery of the patella, with each jaw member having a respective handle, integrally formed therewith, which handles may be pivoted so as to pivot the jaw members to and from engagement with the patella periphery. At the ends of the handles, a locking device is provided therebetween which enables the locking of the jaw members about the patella periphery.

Furthermore, Petersen's saw guide is so designed that the posterior sides of the jaw members are co-planer and these posterior sides of the jaw members define the plane of resection of the patella; and that attached to the saw guide and pivotable on a common axis with the axis of pivoting the jaw members are a series of wing gauges, a plurality of which are located on the posterior side of the saw guide; with a single further guide being located on the anterior side of the saw guide.

The anterior wing gauge is for the purpose of aiding the surgeon in determining whether the patella has been grasped at the correct location so that after resection adequate bone stock will remain. More particularly, the posterior wing gauges are provided so that the saw guide has adjustability; with one of these gauges being placed in a position to engage the most posterior portion of the patella. The anterior gauge is then pivoted into a position to determine if adequate bone stock will remain after resection. If the anterior gauge does not rotate freely, then sufficient bone stock remains.

As indicated hereinabove, saw guides of the type taught by Petersen utilize the co-planer posterior sides of the jaw members to define the plane of resection of the patella. After the patella has been properly positioned within the saw guide and the guide secured thereon, a saw may then be used remove the unwanted bone by manually placing and holding the saw flush against jaw member surfaces defining the aforementioned plane of resection through out the cutting process.

Dunn et al., in U.S. Pat. No. 4,759,350, hereby incorporated by reference for background purposes, describes in considerable detail (with reference to FIGS. 18, 19 and 20), a prior art process for preparing a patella for resection using a saw guide. The guide used is of the type described by Petersen at least in so far as requiring the saw to be manually held in place against the jaw member surfaces defining the aforementioned plane of resection while cutting the bone.

To improve the accuracy of cut over the type of guide devices described by Petersen and Dunn et al., improved saw guides are known which provide an integral saw capture slot within and through the aforementioned jaw members, for receiving and guiding a saw throughout the cutting process. Furthermore, guide devices are known which in addition to providing the aforementioned integral saw capture slot, also provide a rotating calibrated stylus for measuring the position of the patella with respect to the capture slot.

One such device is described by Whitlock et al. in U.S. Pat. No. 5,147,365, hereby incorporated by reference, issued Sep. 15, 1992, where the stylus is not only rotatable, but may also adjusted through displacement upwards and/or downwards before being locked into a desired position, to replace the plurality of wing gauges required by the Petersen type device.

In particular, Whitlock et al., describes a patella osteotomy guide for use by a surgeon in preparing a patella to receive a prosthetic articulating surface on the patella's posterior side.

According to the teachings of Whitlock et al., the guide captures a patella between jaws of a plier-like appliance. The jaws are curved for grasping a patient's patella, with a row of teeth facing inwardly from the jaws. The teeth are generally of pyramid shape, but a vertex of each tooth lies in a plane containing a bottom side of the respective jaw. This offset enables the teeth to grasp the patella in the middle. Each of the jaws has an integral saw capture slot extending along its length through which a sagittal saw may be inserted to precisely remove a selected portion of the patella. The tips of the jaws are extended so that the osteotomy guide may be used with larger patellas.

Furthermore, according to the teachings of Whitlock et al., the aforementioned rotating calibrated stylus accurately measures the position of the patella with respect to the integral saw capture slots. The stylus can be rotated so that a measurement can be made from the highest point of the patella, even if that point is asymmetrical with respect to the rest of the patella.

According to the preferred embodiment of Whitlock et al.'s invention, the rotating stylus also functions as a pivot or fulcrum about which the jaws and handles of the osteotomy guide rotate. Handles for the osteotomy guide are offset from the plane of the jaws to allow hand access without interference with the patellar tendon of the patient. A threaded rod and thumb nut are provided on the handles so that the guide may be clamped to the patella.

Still further, according to the teachings of Whitlock et al., the rotating stylus, as indicated hereinbefore, may be displaced up and down and then locked into a selected position using a draw bar and captured balls, effectively replacing the plurality of wing gauges described in the incorporated Petersen patent.

From a purely mechanical point of view, the rotating adjustable stylus integrated onto the type of guide taught by Whitlock et al., makes such a guide unduly complex, costly and subject to mechanical failure by virtue of the number of parts required to manufacture and use such a guide.

Furthermore, the calibrated stylus contemplated by Whitlock et al., requires the surgeon to visually determine a desired resection depth, and then lock the stylus in place at a prescribed, previously measured, location. The measurement, instrument placement and stylus setting procedures required by Whitlock et al. depend on the surgeon's vision and manual dexterity in operating the stylus, may be inaccurate and would not insure, for example, that a precise amount of bone (for example, precisely 6 mm, 7 mm, etc. of bone), could be removed during a given operation.

Still further, although the stylus arrangement taught by Whitlock et al., may be positioned "out of the way" during the resection process per se (by rotation), the stylus remains as a potential impediment to vision and guide manipulation since it is physically integrated on the guide.

Further yet, guides of the type taught by Whitlock et al. fail to easily accommodate the insertion of the saw into a capture slot. Such guides are potentially dangerous if a mishap should occur when trying to slide the saw into the capture slot, particularly since (at the time the saw is inserted) the patient is "open" and the operation is in progress.

For all of the reasons set forth hereinabove, it would be desirable to provide an easy to use resection guide that is mechanically simple, reliable and which enables a very accurate resection to be performed without having to rely on the surgeon having to measure and then set a desired resection depth using a calibrated stylus of the type described by Whitlock et al., prior to securing the resection guide.

In particular, it would be desirable if no such requirement for taking measurements and then accurately setting the stylus were required within a predetermined range of pre-specified resection depths that are most often used when performing knee surgery, such as a range between 6 mm and 11 mm in 1 mm increments.

Furthermore, it would be desirable to provide a resection guide for which an accurate resection level may be easily set using a quick release stylus that easily attaches to (and may be quickly removed from) calibrated and marked steps on the resection guide, for visibility during resection.

Still further, it would be desirable to provide, in combination with the above desired features, a resection guide that is not only slotted, but also provided with a saw blade insertion guide to help avoid the aforementioned potential for injury if a mishap should occur when trying to slide the saw into the capture slot.

SUMMARY OF THE INVENTION

In view of the foregoing, it is an object of the invention to provide an easy to use and mechanically simple patella resection guide which allows very accurate resections to be repeatedly performed.

It is a further object of the invention to provide a patella resection guide that allows very accurate resections to be repeatedly performed without first having (each time the instrument is used) to measure and then set the desired resection depth using a calibrated adjustable stylus.

It is still a further object of the invention to provide a patella resection guide that allows very accurate resections to be repeatedly performed over a predetermined range of prespecified resection depths that are most often used when performing knee surgery.

Yet another object of the invention is to provide a patella resection guide that accomplishes the aforementioned objects and at the same time does not, by virtue of its structure and operating characteristics, unnecessarily interfere with the surgeons visibility while a resection is being performed.

Further yet, it is an object of the invention is to provide a patella resection guide that may be used to set an accurate resection level in combination with a quick release stylus that easily attaches to (and may be quickly removed from) calibrated and marked steps located on the resection guide itself (not on the stylus); whereby the surgeon's visibility while performing surgery may be enhanced by virtue of the fact that the stylus is removable.

Still further, it is an object of the invention to provide, in combination with the above desired features, a resection guide that is slotted (i.e., includes a saw capture slot) for guiding a saw; and which also is provided with a saw blade insertion guide to help avoid the potential for injury if a mishap should occur when trying to slide the saw into the capture slot.

According to one aspect of the invention, apparatus for guiding a saw used to perform resection of a bone, comprises: (a) means for gripping the bone, including first and second arms pivotally mounted together at a first pivot axis, wherein each of the arms has a handle portion at one end and a jaw member at the other end whereby pivoting of the handle portions towards one another causes the jaw members to pivot toward one another about the pivot axis and into engagement with the periphery of the bone; (b) slot means, formed integrally within the jaw members and defining a plane of resection, for receiving and guiding a saw blade; and (c) means for setting resection depth which includes at least one calibrated and marked step integrally formed as part of at least one of the jaw members.

According to this first aspect of the invention, the means for setting resection depth further comprises a stylus removably attached to the at least one step; and each step has a saw blade insertion guide associated therewith, formed as an integral part of the jaw member on which a given step is located.

According to a preferred embodiment of the invention, the insertion guide extends outward from the periphery of the jaw member on which the given step is located and is integrally formed extension of the slot means.

Furthermore, according to a preferred embodiment of the invention, the means for setting resection depth comprises a plurality of calibrated and marked steps which are spaced over a predetermined range of prespecified resection depths. The steps are all formed as an integral part of the jaw members.

The instruments contemplated by the preferred embodiment of the invention also include adjustable locking means, connected between the aforementioned handle portions, for adjustably locking the relative position of the handle portions and thereby locking the relative position of the jaw members.

According to a further aspect of the invention, apparatus for guiding a saw used to perform resection of a bone, comprises: (a) means for gripping the bone, including first and second arms pivotally mounted together at a first pivot axis, wherein each of the arms has a handle portion at one end and a jaw member at the other end whereby pivoting of the handle portions towards one another causes the jaw members to pivot toward one another about the pivot axis and into engagement with the periphery of the bone; (b) slot means, formed integrally within the jaw members and defining a plane of resection, for receiving and guiding a saw blade; and (c) means for setting resection depth which includes a stylus that is removably attached to at least one of the jaw members.

A still further aspect of the invention is directed to a stylus per se, for use in conjunction with a bone resection saw guide, wherein the saw guide includes first and second arms pivotally mounted together at a first pivot axis, wherein each of the arms has a handle portion at one end and a jaw member at the other end whereby pivoting of the handle portions towards one another causes the jaw members to pivot toward one another about the pivot axis and into engagement with the periphery of the bone to set an accurate resection level, from a set of prespecified resection levels over a predetermined range, where each prespecified resection level corresponds to a calibrated and marked step located on one of the jaw members, comprising: (a) means for contacting an exposed surface of the bone; and (b) means for removably attaching the stylus to a selected step to thereby select and set an accurate resection level from the set of prespecified resection levels.

According to a preferred embodiment of the invention, the aforementioned means for removably attaching further comprises a spring operated stylus engagement means.

The invention features a resection saw guide which allows very accurate resections to be repeatedly performed over a predetermined range of prespecified resection depths that are most often used when performing knee surgery. According to an illustrative embodiment of the invention, the calibrated and marked steps on the guide are set in the range of 6 mm to 11 mm in 1 mm increments.

Furthermore, the invention features the ability to set an accurate resection level, without the need for measuring and then visually attempting to accurately set resection depth, by the use of a quick-release stylus that easily attaches to calibrated and marked steps on the resection guide. A further feature of the invention using the quick release stylus is the improved visibility attained when the stylus is easily removed during resection.

Further features of the invention include the greater saw blade control achieved when performing the resection by virtue of the resection guide being slotted; and the enhanced safety factor achieved by virtue of the saw blade insertion guide making it easier (and thus safer) to insert the saw blade into the slot.

These and other objects, embodiments and features of the present invention and the manner of obtaining them will become apparent to those skilled in the art, and the invention itself will be best understood by reference to the following Detailed Description read in conjunction with the accompanying Drawing.

DETAILED DESCRIPTION

Figure 1:
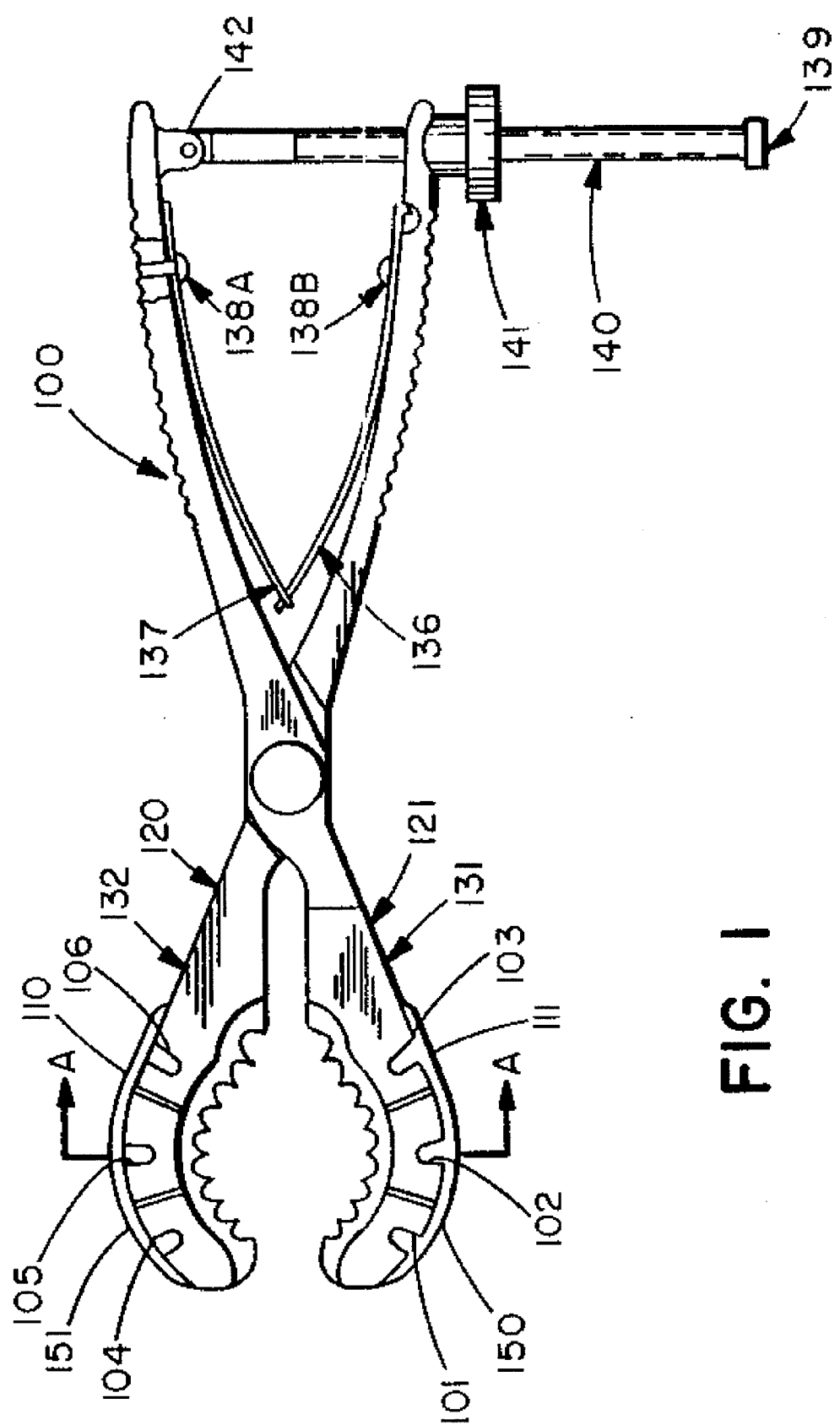
FIG. 1 depicts a top view of the slotted patella resection guide contemplated by a preferred embodiment of the invention.

Reference should now be made to FIG. 1 which, as indicated hereinbefore, depicts a top view of the slotted patella resection guide 100 contemplated by a preferred embodiment of the invention.

Slotted patella resection guide 100 when used in combination with the stylus contemplated by the invention (for example, stylus 400 shown and described in detail hereinafter with reference to FIG. 4) is a device used in the preparation of a human patella to accept a patellar prosthesis in total knee arthroplasty. Guide 100 and stylus 400 used in combination facilitate the accurate placement of the guide at a level to resect a predetermined amount of bone.

The resection guide contemplated by the illustrative embodiment of the invention described shown in FIG. 1 has six slots at various heights above the resection level to accept exemplary stylus 400. In particular, the slots depicted in FIG. 1 (slots 101–106) allow for 6 mm, 7 mm, 8 mm, 9 mm, 10 mm, and 11 mm resections, respectively.

Once the surgeon has determined the amount of bone to be resected, stylus 400, according to the illustrative embodiment of the invention being described herein, is simply inserted into and removably attached to the corresponding slot.

Guide 100 is also employed to hold the patella stable and provide a capture to guide the saw blade.

The instruments depicted in the drawing will now be explained in greater detail in the context of an illustrative example of how they are used to perform the resection of a patella.

The overall patella thickness is first measured. Based on the thickness of the patella the surgeon decides the amount of bone to be resected.

Figure 4:
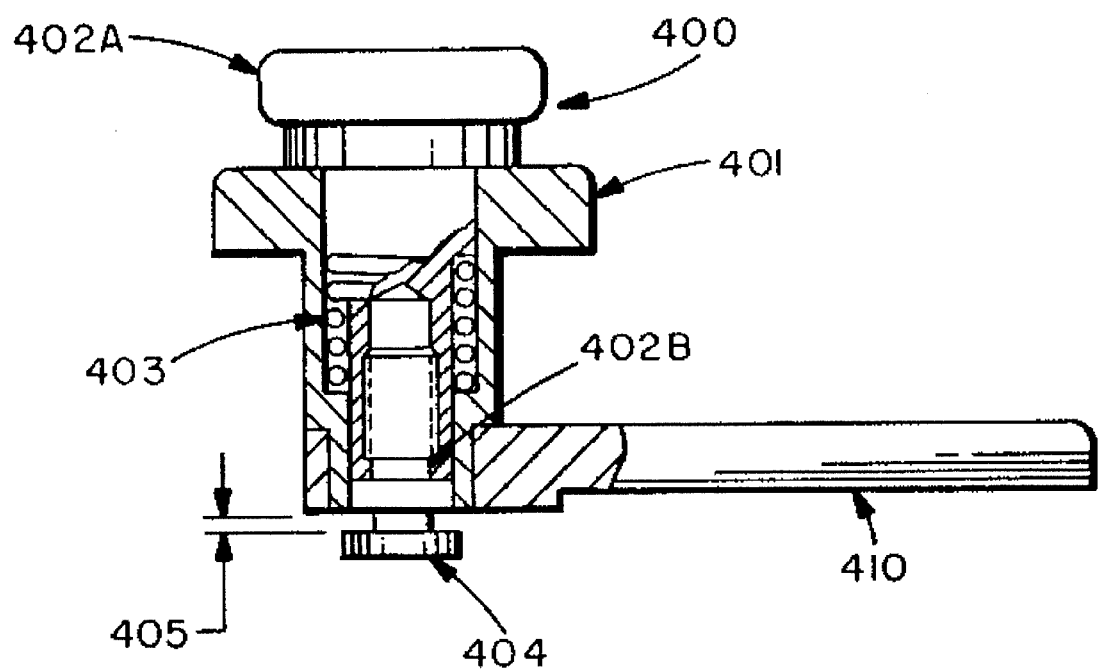
FIG. 4 depicts an example of a removable stylus assembly contemplated by a preferred embodiment of the invention for use in combination with the slotted patella resection guide depicted in FIG. 1.

A quick release stylus, exemplified by stylus 400 depicted in FIG. 4, is then placed in the appropriate marked position on the resection guide to achieve the desired resection level.

Resection guide 100 is then placed on the patella so that the stylus touches the patella in the area where its thickness was measured to establish the depth of cut. Similar procedures (having a stylus touch the patella in the area where thickness was measured) for establishing the depth of cut using a stylus integrally formed as part of prior art resection guides, are explained in detail in the patents previously incorporated herein by reference.

According to the present invention, resection guide 100 is then clamped and locked in place; and stylus 400 is then removed. A saw blade is then introduced into the slotted capture to perform the resection.

By utilizing the illustrative apparatus depicted in FIGS. 1–4, the surgeon is able to accurately and repeatedly (on other patients using the same instruments) perform resections over a predetermined range of prespecified resection depths that are most often used when performing knee surgery; without the need for measuring and then visually attempting to accurately set the saw guide and stylus to obtain a desired resection depth.

Furthermore, as indicated hereinbefore, by using the quick release stylus, a visibility improvement is attained by removing the stylus after the resection saw guide is set.

Figure 2:
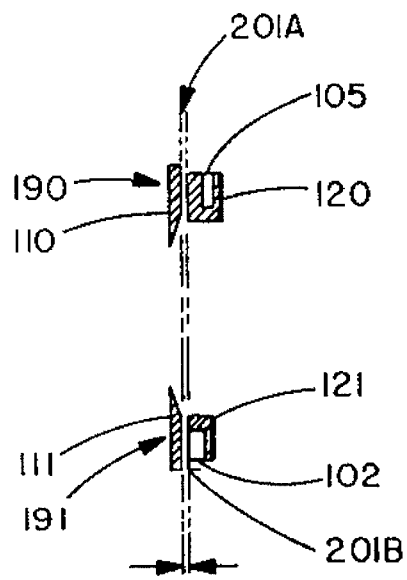
FIG. 2 depicts the portion of the slotted patella resection guide shown in FIG. 1 shown along section A—A.

Still further, as may be seen with reference to FIGS. 1 and 2, greater saw blade control may achieved when performing the resection by virtue of illustrative resection guide 100 being slotted (i.e., including a saw capture slot). The capture slot for achieving saw blade control may best being seen with reference to section A—A of FIG. 1; shown in greater detail in FIG. 2.

In particular, FIG. 2 depicts the portion of the slotted patella resection guide shown in FIG. 1 shown along section A—A as including saw capture slot 201 shown in two portions, 201a and 201b. Capture slot portion 201a is located within jaw member 190 (comprised of lower jaw member portion 110 and upper jaw member portion 120) on resection guide arm 132 (shown in FIG. 1); and capture slot portion 201b is located within jaw member 191 (comprised of lower jaw member portion 111 and upper jaw member portion 121) on resection guide arm 131 (also shown in FIG. 1).

According to a preferred embodiment of the invention, capture slot 201 must be wide enough to enable a saw blade to fit freely thru the slot opening in one jaw (e.g., opening 201a) and pass freely straight thru and into the slot opening in the opposing jaw (e.g.,opening 201b) at maximum spread of the guide jaws.

Furthermore, according to the invention, the enhanced safety factor referred to hereinbefore is achieved by virtue of a saw blade insertion guide (like the illustrative insertion guide shown in the form of "ledges" 150 and 151 extending out from the periphery of lower jaw members 110 and 111), making it easier (and thus safer) to insert the saw blade into the slot. These extensions may be viewed as integrally formed extensions of the slot means formed by illustrative jaws member pairs 110/120 and 111/121.

FIG. 2 further illustrates, in accordance with the teachings of the invention, how the various calibrated and marked steps yield differing resection depths when the guide 100 and stylus 400 combination is used in accordance with the teachings of the invention. In particular, FIG. 2 illustrates that slot 105, located across from slot 102, is formed within upper jaw member 120 to be 3 mm higher than slot 102 in jaw member 121. The result, after stylus 400 is inserted in slot 105 and is used to determine where guide 100 is secured, will be a plane of resection at a depth 3 mm greater than if stylus 400 had been inserted in slot 102.

Figure 3:
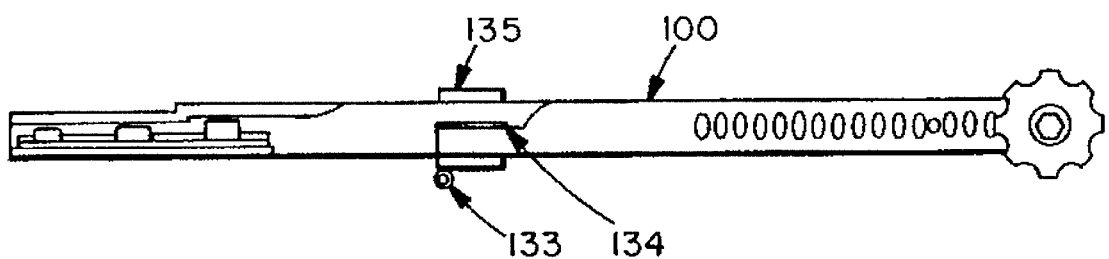
FIG. 3 depicts a side view of the of the slotted patella resection guide depicted in FIG. 1.

Further aspects of saw guide 100 will now be described with reference to FIGS. 1 and 3 (where FIG. 3 depicts a side view of the of the slotted patella resection guide depicted in FIG. 1), to enable those skilled in the art to make and use the invention.

In particular, saw guide 100 is shown in FIG. 1 to include the aforementioned left and right arms, indicated by reference numerals 131 and 132, respectively. The arms are shown fastened together by hinge pin 133, washer 134 and threaded cap 135 (all shown in FIG. 3), where items 133 and 135 are to be tightened such that arms 131 and 132 move freely after welding cap 135 onto the body of guide 100.

Furthermore, with reference to FIG. 1, the illustrative guide 100 may be seen to include male leaf spring 136; female leaf spring 137; two socket button cap screws, shown as screws 138a and 138b, respectively; retaining ring 139; threaded locking rod 140; locking knob 141; and dowel pin 142, all of which provide a mechanism for adjusting guide 100 and locking it in place about a patella once the proper resection depth is chosen.

Reference should now be made to FIG. 4 which depicts an example of a removable stylus assembly contemplated by a preferred embodiment of the invention for use in combination with slotted patella resection guides of the type depicted in FIG. 1.

In particular, FIG. 4 depicts the combination of stylus gauge body 401; a stylus thumb piece, shown in two parts, 402*a* (where thumb pressure may be applied and/or released to respectively release and/or attach the stylus to guide 100), and 402*b* (which, when the thumb piece is in the fully compressed position results in the full dimension shown at 405; compression spring 403; stylus engagement screw 404; and means 410 for contacting an exposed surface of the bone when stylus 400 is in use in conjunction with setting the resection depth for guide 100.

Stylus 400, which operates in cooperation with guide 100 but may be manufactured separately, may thus, according to one aspect of the invention, be characterized as (a) means for contacting an exposed surface of the bone; and (b) means for removably attaching the stylus to a selected step to thereby select and set an accurate resection level from the set of prespecified resection levels.

As indicated hereinbefore, according to a preferred embodiment of the invention, the aforementioned means for removably attaching further comprises spring operated stylus engagement means, such as the engagement means illustrated by way of example in FIG. 4.

What has been described in detail hereinabove are methods and apparatus which meet all of the aforestated objectives. As previously indicated, those skilled in the art will recognize that the foregoing description has been presented for the sake of illustration and description only. It is not intended to be exhaustive or to limit the invention to the precise form disclosed, and obviously many modifications and variations are possible.

The embodiments and examples set forth herein were presented in order to best explain the principles of the instant invention and its practical application to thereby enable others skilled in the art to best utilize the instant invention in various embodiments and with various modifications as are suited to the particular use contemplated.

In view of the above it is, therefore, to be understood that the claims appended hereto are intended to cover all such modifications and variations which fall within the true scope and spirit of the invention.

What is claimed is:

1. Apparatus for guiding a saw used to perform resection of a bone, comprising:
    (a) means for gripping said bone, including first and second arms pivotally mounted together at a first pivot axis, wherein each of said arms has a handle portion at one end and a jaw member at the other end whereby pivoting of said handle portions towards one another causes said jaw members to pivot toward one another about said pivot axis and into engagement with the periphery of said bone;
    (b) guide means, formed integrally within said jaw members and defining a plane of resection, for receiving and guiding a saw blade; and
    (c) means for setting resection depth which includes at least two calibrated and marked steps integrally formed in said means for gripping said bone, whereby a stylus can be removably inserted into a selected one of the at least two steps to set the resection depth.

2. Apparatus as set forth in claim 1 wherein said means for setting resection depth further comprises said stylus removably attached to said selected step.

3. Apparatus as set forth in claim 2 wherein said stylus further comprises spring operated stylus engagement means.

4. Apparatus as set forth in claim 1 wherein each step has a saw blade insertion guide associated therewith.

5. Apparatus as set forth in claim 4 wherein said insertion guide is formed as an integral part of at least one of the jaw members.

6. Apparatus as set forth in claim 5 wherein said insertion guide extends outward from the periphery of the at least one jaw member.

7. Apparatus as set forth in claim 6 wherein said insertion guide is an integrally formed extension of said guide means.

8. Apparatus as set forth in claim 1 wherein said calibrated and marked steps are spaced over a predetermined range of prespecified resection depths.

9. Apparatus as set forth in claim 8 wherein said steps have a saw blade insertion guide associated therewith.

10. Apparatus as set forth in claim 9 wherein said insertion guide is formed as an integral part of said jaw members as an extension of said guide means extending outward from the periphery of said jaw members.

11. Apparatus as set forth in claim 8 wherein said means for setting resection depth further comprises said stylus.

12. Apparatus as set forth in claim 11 wherein said stylus further comprises:
    (a) means for contacting an exposed surface of said bone; and
    (b) means for removably attaching said stylus to a selected step to thereby select and set an accurate resection level from said prespecified resection levels.

13. Apparatus as set forth in claim 12 wherein said means for removably attaching further comprises spring operated stylus engagement means.

14. Apparatus as set forth in claim 1 further comprising adjustable locking means connected between said handle portions for adjustably locking the relative position of said handle portions and thereby locking the relative position of said jaw members.

15. Apparatus for guiding a saw used to perform resection of a bone, comprising:
    (a) means for gripping said bone, including first and second arms pivotally mounted together at a first pivot axis, wherein each of said arms has a handle portion at one end and a jaw member at the other end whereby pivoting of said handle portions towards one another causes said jaw members to pivot toward one another about said pivot axis and into engagement with the periphery of said bone;
    (b) guide means, formed integrally within said jaw members and defining a plane of resection, for receiving and guiding a saw blade; and
    (c) means for setting resection depth which includes at least two calibrated and marked steps integrally formed in said means for gripping said bone and further including a stylus that is removably attachable to said steps.

16. Apparatus as set forth in claim 15 wherein said stylus further comprises spring operated stylus engagement means.

17. Apparatus as set forth in claim 15 wherein at least one of said jaw members further comprises a saw blade insertion guide.

18. Apparatus as set forth in claim 15 further comprising adjustable locking means connected between said handle portions for adjustably locking the relative position of said handle portions and thereby locking the relative position of said jaw members.

* * * * *